United States Patent [19]

König et al.

[11] Patent Number: 5,153,326
[45] Date of Patent: Oct. 6, 1992

[54] PREPARATION OF 4-AMINO-1,2,4-TRIAZOL-5-ONES

[75] Inventors: Klaus König, Odenthal; Klaus-Helmut Müller, Düsseldorf; Lothar Rohe, Wuppertal, all of Fed. Rep. of Germany

[73] Assignee: Bayer Aktiengesellschaft, Leverkusen, Fed. Rep. of Germany

[21] Appl. No.: 690,028

[22] Filed: Apr. 23, 1991

Related U.S. Application Data

[62] Division of Ser. No. 534,402, Jun. 6, 1990, Pat. No. 5,034,538.

[30] Foreign Application Priority Data

Jun. 21, 1989 [DE] Fed. Rep. of Germany ....... 3920270

[51] Int. Cl.⁵ .......................................... C07D 249/12
[52] U.S. Cl. ................................ 548/263.8; 546/276
[58] Field of Search ...................... 548/263.8; 546/276

[56] References Cited

U.S. PATENT DOCUMENTS 4,952,701 8/1990 Muller et al. ................. 548/263.8

*Primary Examiner*—Patricia L. Morris
*Attorney, Agent, or Firm*—Sprung Horn Kramer & Woods

[57] ABSTRACT

A process for the preparation of 4-amino-1,2,4-triazol-5-one of the formula

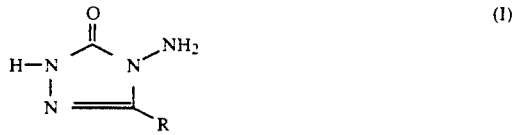

in which
R represents unsubstituted or substituted alkyl, alkenyl, cycloalkenyl, cycloalkyl, aralkyl, aryl or heterocyclyl, which comprises reacting a carbodihydrazide of the formula

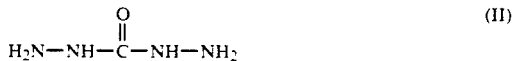

with a nitrile of the formula

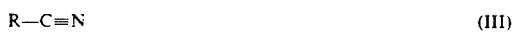

The carbodihydrazide of the formula (II) may be produced in a preliminary stage by reacting a carbonic acid derivative with hydrazine or hydrazine hydrate.

6 Claims, No Drawings

PREPARATION OF 4-AMINO-1,2,4-TRIAZOL-5-ONES

This is a division of application Ser. No. 07/534,402, filed Jun. 6, 1990, now U.S. Pat. No. 5,034,538.

The invention relates to a new process for the preparation of 4-amino-1,2,4-triazol-5-ones, which are intermediate products for the preparation of herbicidal active compounds.

It is known that 4-amino-1,2,4-triazol-5-ones are obtained when carbohydrazide is cyclized with carboxylic acids under the influence of heat (compare Chem. Ber. 98, 3025 [1965]). The disadvantage of this process is that the cyclization only takes place after a relatively long reaction time (10 hours), and self-condensation of the carbohydrazide to give 4-aminourazole also takes place under these conditions. The yields of the desired triazoles are low in this process (16% to 22%).

It is furthermore known that 4-amino-1,2,4-triazol-5-ones are obtained when 1,5-diacyl-carbohydrazides are cyclized in the presence of aqueous alkali. The 1,5-diacylcarbohydrazides required for this are first prepared by heating carbohydrazide with carboxylic acids (compare Chem. Ber. 98, 3025 [1965]). The yields over the two stages are also unsatisfactory in this process.

It is moreover known that 4-amino-1,2,4-triazol-5-ones are obtained when $N^\beta$-acylcarbazic acid esters are reacted with hydrazine hydrate (compare Chem. Ber. 98, 3025 [1965]). A disadvantage of this process is likewise the low yields, especially taking into account the fact that the $N^\beta$-acylcarbazic acid esters required as starting compounds also first have to be prepared Another serious disadvantage of this method is that it renders only certain (3-methyl)-4-amino-1,2,4-triazol-5-ones accessible. Cyclization does not take place with the homologous ethyl compound ethyl $N^\beta$-propionyl-carbazate under the same conditions.

It is furthermore known that 4-amino-1,2,4-triazol-5-ones of the formula (I) described below are obtained when carbohydrazide is cyclized with orthoesters under the influence of heat (compare Chem. Ber. 27, 55 [1894]; J. Prakt. Chem. [2] 52, 454 [1895]; Chem. Ber. 57, 1321 [1924]; Liebigs Ann. Chem. 475, 120 [1929] and Inorganic Synthesis 4, 32 [1953]).

A disadvantage of this process is that orthoesters are required as starting compounds and themselves have to be prepared in a multi-stage synthesis—which proceeds via intermediate stages which are susceptible to hydrolysis—which makes the overall synthesis of little advantage for cost and environmental reasons.

Another known process for the preparation of 4-amino-1,2,4-triazol-5-ones comprises reaction of Pinner salts with carbazic acid esters and subsequent cyclization with hydrazine hydrate (compare Bull. Soc. Chim. France 1962, 1364; Eur. J. Med. Chem. - Chim. Ther. 1983, 215; and Chimica Acta Turcica 7, 269 [1979]). A disadvantage of this process is the low overall yield and the preparation of the Pinner salts, for which reaction times of several days are required and which have to be carried out under strict exclusion of moisture (compare Ber. dtsch. chem. Ges. 16, 1643 [1883]; and Organic Syntheses, Coll. Vol. I, 5 [1951]).

It has now been found that 4-amino-1,2,4-triazol-5-ones of the general formula (I)

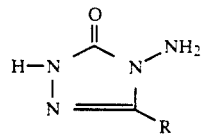

in which
R represents optionally substituted alkyl, alkenyl, cycloalkenyl, cycloalkyl, aralkyl, aryl or heterocyclyl, are obtained in good yields and in a high purity by a process in which carbodihydrazide of the formula (II)

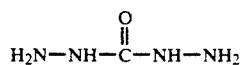

is reacted with nitriles of the general formula (III)

    (III)

in which
R has the abovementioned meaning, if appropriate in the presence of a reaction auxiliary and if appropriate in the presence of a diluent at temperatures between 20° C. and 250° C.

In this process, the carbodihydrazide can either be (a) employed in isolated form or (b) produced in a preliminary step and further reacted in situ.

It is to be described as exceptionally surprising that the reaction according to the invention gives the compounds of the formula (I) in high yields and in a high purity, since according to the known synthesis methods described above, starting substances which are either expensive or expensive to prepare are to be employed or only unsatisfactory yields are achieved.

The process according to the invention has a number of advantages: the starting substances of the formulae (II) and (III) to be employed are inexpensive commercially available materials; they can be reacted and worked up in a relatively simple manner. Improved yields can in general be achieved, compared with the known. process. Finally, it is also possible to prepare aminotriazolones which are not accessible by known processes.

A particular advantage of the process according to the invention lies in the fact that the carbodihydrazide of the formula (II) to be employed as the starting substance not only can be employed as the isolated substance but also alternatively can be produced from inexpensive starting substances in a preliminary reaction by customary methods and can be further reacted in situ, that is to say in a "one-pot process", with compounds of the formula (III).

Formula (I) provides a general definition of the 4-amino-1,2,4-triazol-5-ones to be prepared by the process according to the invention. Compounds of the formula (I) which are preferably prepared by the process according to the invention are those in which
R represents in each case straight-chain or branched alkyl or alkenyl having up to 8 carbon atoms, in each case optionally substituted by $C_3$–$C_6$-cycloalkyl, phenyl, $C_1$–$C_4$-alkoxy, $C_1$–$C_4$alkylamino, di-($C_1$–$C_4$-alkyl)-amino, hydroxyl, amino or halogen, or R represents cycloalkenyl or cycloalkyl having in each case up to 6 carbon atoms, in each case optionally substituted by hydroxyl, amino, halogen, phenyl, $C_1$–$C_4$-alkoxy, $C_1$-$C_4$-alkylamino or di-($C_1$-$C_4$-alkyl)-amino, or R represents benzyl, phenyl, pyridyl or thenyl.

Compounds of the formula (I) which are prepared in particular by the process according to the invention are those in which R represents methyl, ethyl, propyl, isopropyl, butyl, isobutyl, sec-butyl, tert-butyl, pentyl, isopentyl, sec-pentyl, tert-pentyl, cyclopentenyl, cyclohexenyl, cyclopropyl, cyclobutyl, cyclopentyl or cyclohexyl, the radicals mentioned optionally being mono-, di- or trisubstituted by fluorine and/or chlorine, or R represents benzyl or phenyl.

If, for example, carbodihydrazide and pivalonitrile are used as starting substances, the course of the reaction in the process according to the invention can be represented by the following equation:

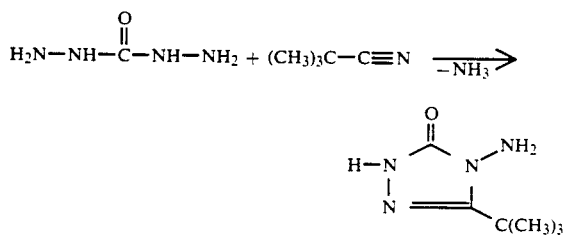

The carbodihydrazide of the formula (II) to be used as a starting substance in the process according to the invention is a known commercially available chemical. The possible preliminary preparation and in situ reaction of this compound is dealt with below.

Formula (III) provides a general definition of the nitriles furthermore to be used as starting substances in the process according to the invention. In formula (III), R preferably or in particular has that meaning which has already been given above as preferred or as particularly preferred for R in connection with the description of the compounds of the formula (I).

Examples which may be mentioned of the starting substances of the formula (III) are: acetonitrile, propionitrile, butyronitrile, isobutyronitrile, valeronitrile, isovaleronitrile, cyclopropanecarbonitrile, cyclobutanecarbonitrile, cyclopentanecarbonitrile, cyclohexanecarbonitrile, cyclohexanecarbonitrile, phenylacetonitrile and benzonitrile.

The starting substances of the formula (III) are known organic synthesis chemicals.

The carbodihydrazide of the formula (II) b used as a starting substance can be prepared in a preliminary stage for carrying out the process according to the invention.

For this, carbonic acid derivatives of the general formula (IV)

in which

X and Y represent the leaving groups customary in carbonic acid chemistry,
are reacted with hydrazine or hydrazine hydrate, if appropriate in the presence of a diluent and if appropriate in the presence of a reaction auxiliary, at temperatures between $-30°$ C. and $+180°$ C., preferably between $-10°$ C. and $+160°$ C.

Suitable leaving groups (X, Y) which may be mentioned for the compounds of the formula (IV) are: halogen, preferably chlorine, amino, straight-chain or branched alkoxy, preferably having 1 to 6 carbon atoms, in particular methoxy or ethoxy, and aryloxy, preferably phenoxy.

X and Y can also together represent straight-chain or branched alkylenedioxy, preferably having 2 to 6 carbon atoms, in particular ethylenedioxy or propylenedioxy.

The carbonic acid derivatives of the formula (IV) can also be constituents of oligomeric or polymeric carbonic acid derivatives, the alcohol component of which is an oxaalkanediol, such as, for example, diethylene glycol.

Examples which may be mentioned of the starting substances of the formula (IV) are:
phosgene, urea, methyl and ethyl chloroformate, dimethyl and diethyl carbonate, diphenyl carbonate, methyl and ethyl carbamate and 2-oxo-1,3-dioxolane ("glycol carbonate") and propylene carbonate.

The starting substances of the formula (IV) are known synthesis chemicals.

The process according to the invention for the preparation of 4-amino-1,2,4-triazol-5-ones is - like the preliminary stage for the preparation of the carbodihydrazide if appropriate—carried out, if appropriate, in the presence of a diluent. Possible diluents here are, in addition to water, practically all the inert organic solvents. These include, preferably, aliphatic and aromatic, optionally halogenated hydrocarbons, such as pentane, hexane, heptane, cyclohexane, petroleum ether, benzine, ligroin, benzene, toluene, xylene, mesitylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, and furthermore diemthyl sulphoxide, tetramethylene sulphone, hexamethylphosphoric triamide and N-methyl-pyrrolidone and finally also alcohols, such as methanol, ethanol, propanol, isopropanol, butanol, isobutanol, sec-butanol, tert-butanol, pentanol, isopentanol, sec-pentanol and tert-pentanol, diols, such as ethane-1,2- diol, propane-1,2-diol and propane-1,3-diol, alkoxyalcohols, such as methoxyethanol and ethoxyethanol, and hydroxyarenes, such as phenol. Phenol and the diols mentioned are particularly preferred as diluents.

The process according to the invention for the preparation of 4-amino-1,2,4-triazol-5-ones is—like the preliminary stage for the preparation of the carbodihydrazide if appropriate—carried out, if appropriate, in the presence of a reaction auxiliary. Possible reaction auxiliaries are in general metal compounds, preferably tin compounds, Examples of these which may be mentioned are: dibutyltin dichloride, dimethyltin dichloride, dibutyltin oxide, hexabutyldistannoxane, butylstannonic acid, dibutyltin dilaurate and dimethyltin oxide.

If "aprotic" diluents, such as, for example N-methyl-pyrrolidone, are used, the use of an "H-acid" compound, such as, for example phenol, ethylene glycol, propylene glycol, diethylamine, dipropylamine or dibutylamine, as a further reaction auxiliary is additionally advantageous.

The reaction temperatures can be varied within a substantial range in the process according to the invention. The reaction is in general carried out at temperatures between 20° and 250°, preferably at temperatures between 60° C. and 200° C.

The process according to the invention is in general carried out under normal pressure. However, it is also possible for it to be carried out under increased or reduced pressure.

For carrying out the process according to the invention, in general between 0.5 and 3 mol, preferably between 0.8 and 1.5 mol, of nitrile of the formula (III) are employed per mol of carbodihydrazide of the formula (II).

In a first preferred variant for carrying out the process according to the invention, the carbodihydrazide of the formula (II) is initially introduced into one of the abovementioned diluents and, after addition of a nitrile of the formula (III) and if appropriate a reaction auxiliary, the mixture is stirred, preferably at elevated temperature between 60° C. and 200° C., until the evolution of ammonia has virtually ended.

To isolate the reaction product of the formula (I), the volatile components are distilled off under reduced pressure. The produce obtained as a solid residue is preferably purified by recrystallization.

In a second preferred variant of the process according to the invention, the carbodihydrazide of the formula (II) is first produced in a preliminary stage from a carbonic acid derivative of the formula (IV) and hydrazine or hydrazine hydrate, preferably by initially introducing hydrazine or hydraxine hydrate into a water bath or ice bath nd slowly metering in the carbonic acid derivative of the formula (V). The reaction mixture is then in general stirred at elevated temperature for several hours. If appropriate, volatile components (such as, for example, water from hydrazine hydrate) are distilled off under reduced pressure and the carbodihydrazide of the formula (II) which remains in the residue is reacted as described above with a nitrile of the formula (III).

The 4-amino-1,2,4-triazole-5-ones of the formula (I) to be prepared by the process according to the invention can be used as intermediate products for the preparation of herbicides (compare US-P 3,884,910 or EP-A 294,666).

PREPARATION EXAMPLES

Example 1 / Compound No. I-1

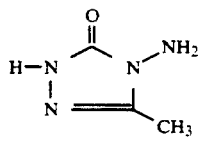

180 g (2.0 mol) of carbodihydrazide are suspended in 360 g of ethylene glycol, and 90 g (2.2 mol) of acetonitrile and 0.5 g of dibutyltin oxide are added at ° C. to 30° C., while stirring The reaction mixture is then heated to a weak reflux (102° C.) and the reflux temperature is then increased to 170° C. in the course of 8 hours. The evolution of ammonia has then virtually ended. The mixture is then concentrated to dryness under reduced pressure (finally under 1 mbar) and the residue is recrystallized from 250 ml of water. 176 g (77% of theory) of 3-methyl-4-amino-1,2,4-triazol-5-one of melting point 225° C. are obtained.

EXAMPLE 2 / Compound No. I-1

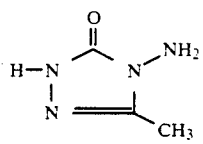

A mixture of 180 g (2.0 mol) of carbodihydrazide, 360 g of N-methyl-pyrrolidone, 90 g (2.2 mol) of acetonitrile and 0.5 of dibutyltin oxide is heated to gentle reflux (122° C.). 65 g of dibutylamine are then added and the reflux temperature is increased to 160° C. in the course of 6 hours, after which the evolution of ammonia has virtually ended. After the volatile constituents have been distilled off, finally under 1 mbar, the residue is recrystallized from 250 ml of water. 150 g (67% of theory) of 3-methyl-4-amino-1,2,4-triazol-5-one of melting point 228° C. are obtained.

Example 3 / Compound No. I-1

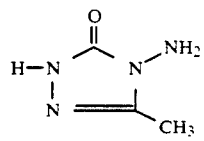

1,354 g (27.1 mol) of hydrazine hydrate are initially introduced into a 6 1 four-necked flask with a contact thermometer, stirrer, dropping funnel, short column and reflux divider, while cooling with ice. 2,898 g (13.5 mol) of diphenyl carbonate in solid form are introduced in the course of 2 hours so that the temperature does no rise about 40° C. by the exothermic reaction which immediately starts. The cooling bath is then removed and the mixture is subsequently stirred at 80° C. for a further 3 hours. Thereafter, the amount of unreacted hydrazine has fallen below 0.4 mol (determined by titration against HCl). The water of hydration is now stripped off under reduced pressure, and 428 g of phenol are also striped off under a full waterpump vacuum (bottom temperature about 105° C.). After the vacuum has been eliminated with nitrogen, 610 ' g (14,9 mol) of acetonitrile are stirred in via the dropping funnel at the same temperature, after which some of the carbodihydrazide formed precipitates but the batch still remains readily stirrable. The temperature is gradually increased by gently supplying heat, and acetonitrile reflux (adjustment of the reflux divider to complete reflux) starts at a bottom temperature of 118° C.; weak evolution of NH₃ starts. The stream of gas is led via a safety wash bottle and a non-return valve into prepared portions of dilute sulphuric acid (indicator bromophenol blue) and the progress of the reaction is monitored in this way. In the course of 18 hours, the bottom temperature rises to 136° C. by the decrease of acetonitrile and the HN₃ evolution becomes increasingly more vigorous. After a further 3 hours (bottom temperature now 150° C.), half of the theoretical amount of ammonia has been split off. The temperature is increased further and after a further 4 hours (temperature 170° C) 80% of the NH₃ has been liberated. The batch is stirred at 180° C. for a further 6 hours and the amount of NH₃ is then 98% of theory. First low-boiling components and then phenol are now distilled off under reduced pressure.

The pressure is adjusted so that the bottom temperature is constantly 160° C.–180° C., under vigorous distillation. Premature crystallization of the end product is in this way avoided. When 80–85% of the phenol has been distilled off, the heating and stirrer are switched off and the pressure is reduced quickly to 15 mbar, residual phenol distilling off and the batch solidifying as crystals. After cooling, the contents of the flask are dissolved by boiling with 1,800 ml of water.

Small residual amounts of phenol are now driven off by distilling off 350 ml of water, 82 g (1.1 mol) of diethylamine are metered in at 80° C., excess diethylamine (0.4 mol) are separated off by incipient distillation and the clear yellowish solution is poured into a glass beaker. After cooling to 10° C., the aminotriazolone which has crystallized out is filtered off with suction, washed with 500 ml of cold aqueous ethanol and dried at 100° C. in vacuo. 1,102 g (71% of theory) of 3-methyl-4-amino-1,2,4-triazol-5-one of melting point 230° C. are obtained.

Example 4 / Comoound No. I-1

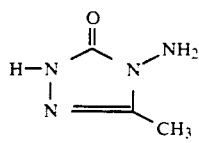

1,270 g of phenol are heated to 80° C. and 810 g (13.5 mol) of urea and 1,350 g (27 mol) of hydrazine hydrate are added. During further heating of the mixture, ammonia is split off vigorously at from 110° C. The temperature is increased to 125° C. in the course of 4 hours; 13.5 mol of ammonia are collected in dilute sulphuric acid. The evolution of gas then subsides, because the ammonia is also being returned-with the water flowing back, and an equilibrium thus develops. Water and ammonia are now distilled off under 50% reflux and the temperature is increased continuously. A bottom temperature of 150° C. is reached in the course of 5 hours, during which 800 g are distilled off, containing 12.15 mol of ammonia, 24.3 mol of water and 3 mol of hydrazine. The mixture is now topped up with 3.5 mol of hydrazine and heated to 140° C. Continuous reflux is maintained by dropwise addition of 554 g (13.5 mol) of acetonitrile (initial amount about 100 ml) at 130°–140° C. All the acetonitrile can be added in this way in the course of 7 hours; 8 mol of NH₃ are formed during this reaction. 160° C. is reached in the course of a further 7 hours, under reflux, and the total amount of eliminated ammonia is increased to 39 mol (96.3% of theory). The phenol is now distilled off as in Example 3 and the residue is dissolved in 1,750 ml of water. Traces of phenol are removed by incipient distillation. After cooling to 10° C., the product is filtered off with suction, washed with cold 50% strength ethanol and dried. 926 g (60% of theory) of 3-methyl-4-amino-1,2,4-triazol-5-one of melting point 230° C. are obtained.

Example 5 / Compound No. I-1

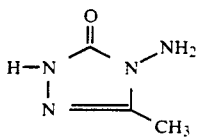

A mixture of 1,175 g of phenol, 1,113 g (12.5 mol) of ethyl carbamate and 1,250 g (25 mol) of hydrazine hydrate is heated to the reflux (bottom temperature 117° C.). During this procedure, 3 mol of ammonia are liberated in the course of 90 minutes; the evolution of gas then subsides. A mixture of alcohol, water, ammonia and hydrazine is now distilled off under a reflux of 75%, the temperature being increased continuously. After 6 hours, 160° C. is reached. About 1,100 g have then distilled off, containing 22.5 mol (90% of theory) of water, 10 mol (80% of theory) of ethanol, 7 mol (56% of theory) of ammonia and 2 mol of hydrazine.

The mixture is now topped up with 2 mol of hydrazine hydrate at 80° C., 513 g (12.5 mol) of acetonitrile are added and the mixture is stirred under a weak reflux. After 7 hours (bottom temperature 140° C.), a further 102 g of acetonitrile (2.5 mol) are added. After 15 hours, a final temperature of 160° C is reached. The evolution of NH₃ subsides. The mixture is worked up as in Example 4. 880 g (62% of theory) of 3-methyl-4-amino-1,2,4-triazol-5-one of melting point 230° C. are obtained.

Example 6 / Compound No. I-1

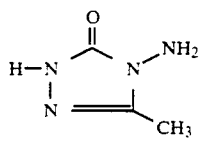

A mixture of 1,650 g of phenol, 1,150 g (23 mol) of hydrazine hydrate and 1,298 g (11 mol) of diethyl carbonate is heated under reflux for 30 minutes. Alcohol, water and 1.5 mol of hydrazine are then distilled off up to a bottom temperature of 160° C. under a reflux of 75%. After cooling to 80° C., 1 g of dibutyltin oxide and 451 g (11 mol) of acetonitrile are added and the mixture is heated to the reflux (120° C.). The temperature can be increased to a limited degree to 160° C. by the decrease in the acetonitrile content in the course of 8 hours. The evolution of gas has then ended. After small amounts of water, alcohol and acetonitrile have been distilled off, phenol is distilled off as in Example 3 and the residue is recrystallized from 900 ml of H₂O. 770 g (61% of theory) of 3-methyl-4-amino-1,2,4-triazol-5-one of melting point 230° C. are obtained.

Example 7 / Compound No. I-2

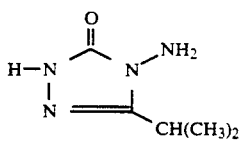

Analogously to Example 3, a solution of carbodihydrazide in phenol is prepared from 2,264 g (10.6 mol) of diphenyl carbonate and 1,058 g (21.2 mol) of hydrazine hydrate and is substantially dehydrated under reduced pressure. After addition of 1 g of dimethyltin oxide and 803 g (11.6 mol) of isobutyronitrile, the mixture is heated under reflux for 10 hours (initial temperature 138° C., final temperature 185° C.). The volatile components are then distilled off under reduced pressure and the residue is dissolved in 1.5 l of hot water. 116 g (1.6 mol) of diethylamine are added at 80° C. and the amine which has not been consumed and residual phenol are then distilled off. After cooling to 10° C., the product is filtered off with suction, washed with cold water and dried. 1,129 g (75% of theory) of 3-isopropyl-4-amino-1,2,4-triazol-5-one of melting point 172° C. are obtained.

Example 8 / Compound No. I-3

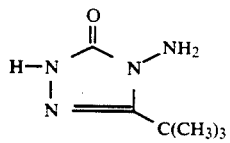

Analogously to Example 3, a solution of carbodihydrazide in phenol is prepared from 1.,900 g (38 mol) of hydrazine hydrate and 4,066 g (19 mol) of diphenyl carbonate and freed from the water of hydration. After the water, 1,600 ml of phenol are also distilled off in vacuo for better utilization of the space. The vacuum is eliminated with nitrogen at 80° C. and 30 g of dibutyltin dichloride and 1,577 g (19 mol) of pivalonitrile are then added. On heating, vigorous evolution of $NH_3$ starts at 125° C. After reflux for 5 hours, a further 158 g (1.9 mol) of pivalonitrile are added and the mixture is heated up to 180° C. in the course of 4 hours. The evolution of gas has then ended. The mixture is now evaporated to dryness analogously to Example 3 and the residue is dissolved in 3 l of hot dimethylformamide. After cooling to 10° C., filtration with suction, washing with cold water and drying at 150° C. in vacuo, 1,703 g (57.4% of theory) of the triazolone of melting point 248° C. are obtained. A further 320 g (10.8% of theory) are obtained by pouring the mother liquor into ice-water and isolating the precipitate formed. Total yield: 2,023 g (68% of theory) of 3-tert-butyl-4-amino-1,2,4-triazol-5-one.

Example 9 / Compound No. I-4

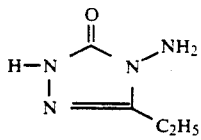

Analogously to Example 3, a solution of carbodihydrazide in phenol is prepared from 3,200 g (64 mol) of hydrazine hydrate and 6,848 g (32 mol) of diphenyl carbonate and the water of hydration and also 1,500 ml of phenol are then distilled off. After addition of 3 g of dimethyltin oxide and 1,848 g (33.6 mol) of propionitrile, the mixture is heated to a weak reflux (125° C.). The temperature can be increased to 180° C. in the course of 11 hours under a continuous reflux. Thereafter, the evolution of $NH_3$ has ended. Phenol is now distilled off at a bottom temperature of 160° C. under reduced pressure (decreasing to 15 mbar), the residue remaining liquid. Residual phenol is therefore removed under 1 mbar using an oil pump. After cooling, the residue is dissolved in 3 l of hot water. 80 ml of diethylamine and 10 g of tartaric acid (to remove a slight turbidity caused by the catalyst) are added to the solution. A diethylamine excess and traces of phenol are removed by incipient distillation. After cooling to 10° C., the product is filtered off with suction, washed with 500 ml of cold 50% strength ethanol and dried at 100° C. in vacuo. 3,478 g (85% of theory) of 3-ethyl-4-amino-1,2,4-triazol-5-one of melting point 171° C. are obtained.

Example 10/ Compound No. I-5

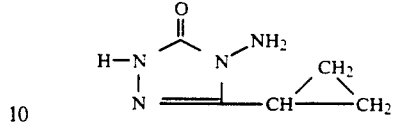

Analogously to Example 3, a solution of carbodihydrazide in phenol is prepared from 1,100 g (22 mol) of hydrazine hydrate and 2,354 g (11 mol) of diphenyl carbonate and dehydrated. 0.5 g of dibutyltin oxide, 774 g (11.5 mol) of cyclopropyl cyanide and 100 ml of petroleum ether (boiling range 80° C.–90° C.) are added at 80° C. The mixture is heated under reflux for 5 hours (initial temperature: 130° C., final temperature 170° C.). Volatile components are distilled off in vacuo and the residue is dissolved in 2 l of water. After addition of 38 ml of diethylamine of 5 g of tartaric acid, the mixture is subjected to incipient distillation and, after cooling, the product is filtered off with suction. 1,172 g (80% of theory) of 3-cyclopropyl-4-amino-1,2,4-triazol-5-one of melting point 183° C. are obtained.

Example 11/Compound No. I-1

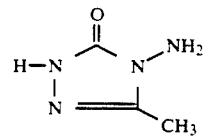

400 g (8 mol) of hydrazine hydrate are added to a mixture of 704 g (8 mol) of glycol carbonate and 300 g of ethylene glycol, while cooling with water, and the mixture is stirred at 50° C. for 60 minutes. 131 g of water are then distilled off under a waterpump vacuum. After addition of a further 400 g (8 mol) of hydrazine hydrate, 361 g (8.8 mol) of acetonitrile and 1 g of dibutyltin oxide, the mixture is heated under reflux for 60 hours and then worked up as in Example 10. 574 g (63% of theory) of 3-methyl-4-amino-1,2,4-triazol-5-one of melting point 231° C. are obtained.

Example 12 / Compound No. I-1

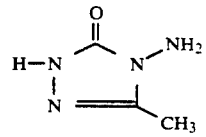

Analogously to Example 3, a solution of carbodihydrazide in phenol is prepared from 1,300 g (26 mol) of hydrazine hydrate and 2,782 (13 mol) of diphenyl carbonate and dehydrated. After addition of 560 g (13.65 mol) of acetonitrile and 2 g of dibutyltin oxide the mixture is stirred at 100° C. for 70 hours and then heated up rapidly to 160° C. Working up analogously to Example 3 gives 1,126 g (76% of theory) of 3-methyl-4-amino-1,2,4-triazol-5-one of melting point 231° C.

It will be understood that the specification and examples are illustrative but not limitative of the present invention and that other embodiments within the spirit and scope of the invention will suggest themselves to those skilled in the art.

We claim:

1. A process for the preparation of a 4-amino-1,2,4-triazol-5-one of the formula

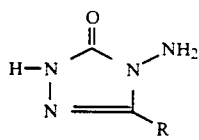

in which

R represents in each case straight-chain or branched alkyl or alkenyl having up to 8 carbon atoms, the alkyl or alkenyl in each case being unsubstituted or substituted by $C_3$-$C_6$-cycloalkyl, phenyl, $C_1$-$C_4$-alkoxy, $C_1$-$C_4$-alkylamino, di-($C_1$-$C_4$-alkyl)-amino, hydroxy, amino or halogen, or R represents cycloalkenyl or cycloalkyl having in each case up to 6 carbon atoms, the cycloalkenyl or cycloalkyl in each case being unsubstituted or substituted by hydroxyl, amino, halogen, phenyl, $C_1$-$C_4$-alkoxy, $C_1$-$C_4$-alkylamino or di-($C_1C_4$-alkyl)-amino, or R represents benzyl, phenyl, pyridyl or thienyl, which comprises (A) reacting a carbonic acid derivative of the formula

in which

X and Y in each case represent halogen, amino, straight-chain or branched $C_{1-6}$-alkoxy, phenoxy; or X and Y together represent straight-chain or branched $C_{2-6}$-alkylenedioxy, with hydrazine or hydrazine hydrate to form a carbodihydrazide of the formula

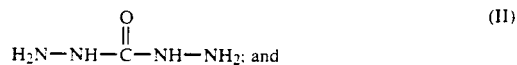

and (B) reacting the carbodihydrazide of the formula (II) with a nitrile of the formula

in situ.

2. The process according to claim 1 in which R represents methyl, ethyl, propyl, isopropyl, butyl, isobutyl, sec-butyl, tert-butyl, pentyl, isopentyl, sec-pentyl, tert-pentyl, cyclopentenyl, cyclohexenyl, cyclopropyl, cyclobutyl, cyclopentyl or cyclohexyl, which are in each case unsubstituted or mono-, di- or trisubstituted by substituents independently selected from the group consisting of fluorine and chlorine, or R represents benzyl or phenyl.

3. The process according to claim 1, wherein the reaction is carried out at a temperature between about 20° C. to about 250° C.

4. The process according to claim 1, wherein between about 0.5 to about 3 mol of nitrile of formula (III) are employed per mol of carbodihydrazide of the formula (II).

5. The process according to claim 1, wherein the reaction is carried out in the presence of a reaction auxiliary, which is a metal compound selected from the group consisting of dibutyltin dichloride, dimethyltin dichloride, dibutyltin oxide, hexabutyldistannoxane, butylstannonic acid, dibutyltin dilaurate and dimethyltin oxide.

6. The process according to claim 1, wherein the reaction is carried out in the presence of an aprotic diluent and a reaction auxiliary, which is a H-acid compound selected from the group consisting of phenol, ethylene glycol, propylene glycol, diethylamine, dipropylamine and dibutylamine.

* * * * *

UNITED STATES PATENT AND TRADEMARK OFFICE
CERTIFICATE OF CORRECTION

PATENT NO. : 5,153,326

DATED : October 6, 1992

INVENTOR(S) : Konig et al.

It is certified that error appears in the above-identified patent and that said Letters Patent is hereby corrected as shown below:

Col. 11, line 19   After " $C_3$ " delete " 14 "

Signed and Sealed this

Third Day of May, 1994

*Attest:*

BRUCE LEHMAN

*Attesting Officer*   *Commissioner of Patents and Trademarks*